United States Patent [19]

Maxwell et al.

[11] 4,001,433
[45] Jan. 4, 1977

[54] QUATERNARY AMMONIUM COMPOUNDS USEFUL AS ANTIFIBRILLATORY AGENT

[75] Inventors: Robert Arthur Maxwell, Armonk, N.Y.; Frederick Charles Copp, London, England

[73] Assignee: Burroughs Wellcome Co., Research Triangle Park, N.C.

[22] Filed: Apr. 1, 1974

[21] Appl. No.: 457,229

Related U.S. Application Data

[62] Division of Ser. No. 48,489, June 22, 1970, abandoned.

[30] Foreign Application Priority Data

July 23, 1969 United Kingdom ............. 31686/69
Dec. 4, 1969 United Kingdom ............. 59230/69

[52] U.S. Cl. ............................................... 424/329
[51] Int. Cl.$^2$ ...................................... A61K 31/14
[58] Field of Search .................................... 424/329

[56] References Cited
FOREIGN PATENTS OR APPLICATIONS
912,949  12/1962  United Kingdom

OTHER PUBLICATIONS

Jones et al., Chem. Abst. vol. 58 (1963) 464e.
Saijo, Studies on Antihistamine Agents vol. 72, pp. 1444–1447.
Dvornik et al., Biochemical Pharmacology, 1963, vol. 12, pp. 229–240, Pergamon Press Ltd., Great Britain.

Primary Examiner—Albert T. Meyers
Assistant Examiner—Allen J. Robinson
Attorney, Agent, or Firm—Dike, Bronstein

[57] ABSTRACT

Compounds containing the N-m-methoxybenzyl-N,N-dimethyl-N-2-hydroxyethylammonium cation and non-toxic salts of the N-m-methoxybenzyl-N,N-dimethyl-N-ethylammonium cation.

The compounds have antiarrhythmic properties, and are useful specifically as antifibrillatory agents.

27 Claims, No Drawings

QUATERNARY AMMONIUM COMPOUNDS USEFUL AS ANTIFIBRILLATORY AGENT

This is a division of application Ser. No. 48,489, filed on June 22, 1970, now abandoned.

This invention relates to compounds useful in the treatment of arrhythmia.

It has previously been proposed to employ the powerful hypotensive drug bretylium (N-o-bromobenzyl-N-ethyl-N,N-dimethylammonium) p-toluenesulphonate in the treatment of cardiac arrhythmia (see "Antiarrhythmic Action of Bretylium", NATURE, Volume 207, No. 4993, pages 203–204, July 10, 1965 and "Treatment of Ventricular Fibrillations and other Acute Arrhythmias with Bretylium Tosylate", The American Journal of Cardiology, April 1968, Volume 21, No. 4, pages 530–543). The drug has potent antiarrhythmic properties but the hypotensive action attributable to sympathetic blockage causes an undesirable substantial lowering of the blood pressure. Thus, it is essential, when the drug is used, for the patients to be in intensive-care units of hospitals.

It has now been found that compounds containing the N-m-methoxy-benzyl-N,N-dimethyl-N-ethylammonium cation or the N-m-methoxy-benzyl-N,N-dimethyl-N-2-hydroxyethylammonium cation possess unexpected advantages over that drug in the treatment of arrhythmia. These compounds not only have antiarrhythmic properties comparable to bretylium, but also significantly less sympathetic blocking action, thus making possible the treatment of heart disorders with little or no adverse effect on blood pressure.

Among the types of arrhythmias which the compounds of this invention are effective in suppressing are ventricular fibrillations and atrial fibrillations. It has been found that an effective amount of the compounds, which are most desirably pharmacologically and pharmaceutically acceptable salts according to this invention, may be used to treat and suppress ventricular and atrial fibrillations in mammals, such as humans, dogs, cats and the like.

In one aspect the present invention provides compounds containing the N-m-methoxybenzyl-N,N-dimethyl-N-2-hydroxyethylammonium cation.

In another aspect the present invention provides a pharmaceutical composition comprising a compound containing the N-m-methoxybenzyl-N,N-dimethyl-N-ethylammonium cation or the N-m-methoxybenzyl-N,N-dimethyl-N-2-hydroxyethylammonium cation, in association with a therapeutically acceptable carrier.

In a further aspect the present invention provides a method of treatment of arrhythmia which comprises the administration of an effective amount of a compound containing the N-m-methoxybenzyl-N,N-dimethyl-N-ethyl-ammonium cation or the N-m-methoxybenzyl-N,N-dimethyl-N-2-hydroxyethylammonium cation to the patient.

The activity resides in the quaternary ammonium cation, the nature of the anion only being important for administration requirements. Administration of the compounds will often be over a prolonged period and in such cases the anion must be pharmacologically acceptable, that is, non-toxic, "non-toxic" meaning having no harmful effect on the patient after prolonged treatment, and as used herein the term "non-toxic" has this meaning. Bromides and iodides of quaternary ammonium compounds have physiological activity inherent in their anions which may be undesirable especially upon prolonged administration.

Accordingly, in another aspect the invention provides non-toxic salts of the N-m-methoxybenzyl-N,N-dimethyl-N-ethylammonium cation or the N-m-methoxybenzyl-N,N-dimethyl-N-2-hydroxymethylammonium cation.

Salts which are especially preferred for therapeutic use are the chlorides, sulphates and sulphonates such as the p-toluenesulphonate.

The compounds in the present invention are quaternary ammonium salts and are most usually prepared by a quaternization reaction. In another aspect of the present invention provides a method for the preparation of the acceptable salts of the N-m-methoxybenzyl-N,N-dimethyl-N-ethylammonium cation and for the preparation of the salts of the N-m-methoxybenzyl-N,N-dimethyl-N-2-hydroxyethylammonium cation by quaternization of an appropriate tertiary amine. The quaternization reactions by which they may be produced are set out below.

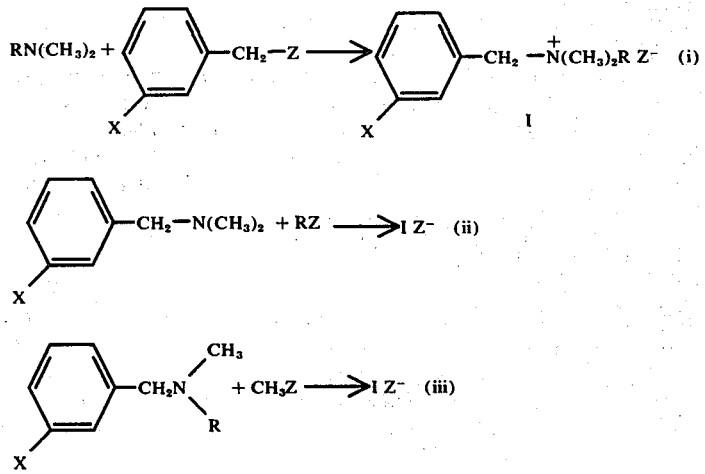

In these reactions and below, the symbol R is the ethyl or the 2-hydroxyethyl group, the symbol X is the methoxy group, and the symbol Z represents a nucleophilic group, for example, a chlorine atom or a sulphate or a sulphonate group.

The compounds in the present invention may also be formed by reacting an appropriate secondary amine with two equivalents of a methylating agent.

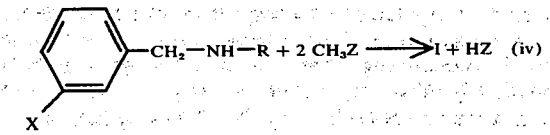

In this reaction, the tertiary amine used in reaction (iii) is formed in situ.

Reactions (i), (ii) and (iii) may be effected in a solvent, for example, acetone, methylethyl ketone, ethyl acetate, methanol, benzene or ether. The reaction (iv) is most advantageously effected in the presence of an acid binding agent, for example, an alkaline salt such as sodium or potassium carbonate.

The salts of the present invention may also be formed from other salts by double decomposition; the non-toxic salts of the present invention may be formed thus from a salt not suitable for prolonged administration.

The present invention also provides the above methods of preparation of the salts of formula I, wherein R is the 2-hydroxyethyl group and X is the methoxy group, and the non-toxic salts of formula I, wherein R is the ethyl group and X is the methoxy group.

The compounds in the present invention may be presented in any acceptable pharmaceutical composition. Compositions for oral or parenteral administration are preferred. Parenteral administration is especially preferred.

For oral administration, fine powders or granules of the compounds may contain diluting, dispersing and/or surface active agents, and may be presented in a draft in water or in a syrup, in capsules or cachets in the dry state or in a non-aqueous suspension, when suspending agents may be included; in tablets, when binders and lubricants may be included; or in a suspension in water, a syrup, an oil or a water/oil emulsion. Where desirable or necessary flavouring, preserving, suspending, thickening or emulsifying agents can be included. Tablets and granules are preferred, and these may be coated.

For parenteral administration, the compounds may be presented in aqueous injection solutions which may contain antioxidants, buffers, bacteriostats, agents which solubilise a relatively insoluble compound, and solutes which render the salt isotonic with the blood; in aqueous suspensions when suspending and thickening agent may also be included; or in non-aqueous solutions and suspensions if the particular compound selected is affected by water.

Dosages are preferably in the range 1 to 10 mg/kg. of the cation. Desirably the pharmaceutical compositions are presented in unit dosage form, usually containing in the range 100 to 600 mg. of cation.

The following examples illustrate the invention.

EXAMPLE 1

N-m-Methoxybenzyl-N,N-dimethylamine (80 g.) was combined with acetone (396 ml.) and ethyl p-toluene sulphonate (m.p. 30.5° C) (105 g.), and the mixture refluxed overnight. The reaction mixture was then cooled to 10° C and the slurry of crystals filtered. A crude product (106 g) was isolated melting at 101.5°–102° C. Recrystallisation from acetone (450 ml.) gave 98 g. of a product melting at 102.5° to 104° C. The product occurred as white needles very soluble in water and alcohol, and gave the following analysis:

|   | Calculated | Found |
|---|---|---|
| C | 62.4 | 62.03 |
| H | 7.45 | 7.50 |
| N | 3.835 | 3.77 |

EXAMPLE 2

A column of Amberlite resin IRA400 (chloride form) was prepared from resin (~25 ml.) and water. It was washed with 2 N-sodium hydroxide until the elute was alkaline (~70 ml.) and then with water until the washings were neutral. A solution of p-toluenesulphonic acid (22 g.) in water (100 ml.) was then poured down the column, when the elute finally became acid. This column was then washed with water until the washings were virtually neutral (about 300 ml. water was required). A solution of N-ethyl-N-m-methoxybenzyl-N,N-dimethylammonium iodide (320 mg.) in water (5 ml.) was then poured down the column and the solution collected in aliquots of 6 ml., each of which was separately evaporated to dryness in a rotatory evaporator. After a total of 36 ml. of washing no more product resulted. The batches of solid (300 mg.) were recrystallised from acetone to give N-ethyl-N-m-methoxybenzy-N,N-dimethylammonium p-toluenesulphonate (280 mg.), m.p. 101°–104° C.

EXAMPLE 3 m-Methoxybenzyl chloride (25 g.) was added slowly to a hot stirred solution of methylaminoethanol (31 g.) in benzene (63 ml.). After heating on a steam-bath for 1 hour, the resulting mixture was cooled and treated with 5N-sodium hydroxide (50 ml.). The aqueous layer was separated and extracted with ether (100 ml.). The combined organic layers were washed with water, dried over anhydrous potassium carbonate, filtered and evaporated. The residue was distilled in vacuo to give N-2-hydroxyethyl-N-m-methoxybenzyl-N-methylamine as a colourless oil, b.p. 116°–118°/0.2 mm.

Methyl iodide (3 ml.) was added to a solution of the above base (5 g.) in ethyl methyl ketone (25 ml.). The mixture warmed spontaneously and oil separated, which subsequently crystallised. The resulting solid, N-m-methoxybenzyl-N,N-dimethyl-N-2-hydroxyethylammonium iodide, was collected and recrystallised from acetone or isopropanol, m.p. 95°–96°.

EXAMPLE 4

Tablets (0.505 g.) of N-m-methoxybenzyl-N,N-dimethyl-N-ethylammonium p-toluene sulphate were made by granulating the salt (0.5 g.) in a fine powder with equal parts of alcohol and water. Magnesium stearate (0.005 g.) as a lubricant was added, and the mixture compressed directly.

EXAMPLE 5

Tablets (0.555 g.) of N-m-methoxybenzyl-N,N-dimethyl-N-2-hydroxyethylammonium iodide were made by mixing the salt (0.25 g.) in a fine powder with lactose (0.25 g.) and starch (0.05 g.), granulating the mixture with alcohol or alcoholic polyvinyl pyrrolidine or a mixture of equal parts of alcohol and water, drying the granules at 40° C, adding magnesium stearate (0.005 g.) and compressing the mixture.

EXAMPLE 6

Tablets (0.208 g.) of N-m-methoxy-N,N-dimethyl-N-2-hydroxyethylammonium iodide were made by granulating the salt (0.1 g.) in a fne powder and lactose (0.1 g.) with gelatin (0.005 g.) in equal parts of alcohol and water. Magnesium stearate (0.003 g.) as a lubricant was added, and the mixture compressed directly.

EXAMPLE 7

Injection preparations of a solution containing N-m-methoxybenzyl-N,N-dimethyl-N-ethylammonium p-toluene sulphonate in Water for Injection (0.1 g. per c.c.) were made by autoclaving the solution at 15 lb. steam pressure for 30 minutes in unit dose ampoules or in multidose containers. For the latter, the Water for Injection contained benzyl alcohol (1%), phenol (0.5%) or chlorocresol (0.1%).

EXAMPLE 8

Injection solutions containing N-m-methoxy-N,N-dimethyl-N-2-hydroxyethylammonium iodide in Water for Injection (0.2 g. per ml.) were made by autoclaving the solution at 15 lb. steam pressure for 30 minutes in unit dose ampoules or multidose containers. For the latter, the Water for Injection contained benzyl alcohol (1.0%), phenol (0.5%) or chlorocresol (0.1%).

We claim:

1. A method for the treatment or suppression of cardiac arrhythmias in a mammal which has had cardiac arrhythmias and which is in need of said treatment or suppression comprising the administration to said mammal of a non-toxic, effective anti-arrhythmic treatment or suppression amount of a pharmaceutically acceptable non-toxic salt of the N-m-methoxybenzyl-N,N-dimethyl-N-ethyl-ammonium cation.

2. The method of claim 1 in which the arrhythmias are ventricular arrhythmias.

3. The method of claim 1 in which the arrhythmias are atrial arrhythmias.

4. The method of claim 1 in which the arrhythmias are atrial or ventricular arrhythmias and the amount is 1 to 10 mg. based on the cation.

5. The method of claim 4 in which the mammal is a human.

6. The method of claim 5 in which the salt is parenterally or orally administered.

7. The method of claim 1 in which the mammal is a human.

8. The method of claim 1 in which the salt is parenterally or orally administered.

9. The method of claim 1 in which the salt is parenterally or orally administered and the mammal is a human.

10. The method of claim 1 in which the salt is a chloride, sulphate or sulphonate salt.

11. A method for the treatment or suppression of cardiac arrhythmias in a mammal which has had a cardiac arrhythmias and which is in need of said treatment or suppression comprising the administration to said mammal of a non-toxic, effective anti-arrhythmic treatment of suppression amount of a pharmaceutically acceptable non-toxic salt of the N-m-methoxybenzyl-N,N-dimethyl N-2-hydroxyethylammonium cation.

12. The method of claim 11 in which the arrhythmias are ventricular arrhythmias.

13. The method of claim 11 in which the arrhythmias are atrial arrhythmias.

14. The method of claim 11 in which the arrhythmias are atrial or ventricular arrhythmias and the amount is 1 to 10 mg. based on the cation.

15. The method of claim 14 in which the mammal is a human.

16. The method of claim 15 in which the salt is parenterally or orally administered.

17. The method of claim 11 in which the mammal is a human.

18. The method of claim 11 in which the salt is parenterally or orally administered.

19. The method of claim 11 in which the salt is parenterally or orally administered and the mammal is a human.

20. The method of claim 11 in which the salt is a chloride, sulphate or sulphonate salt.

21. A pharmaceutical composition in dosage form adapted for administration to treat or suppress cardiac arrhythmias comprising per dosage unit an effective cardiac arrhythmia treatment or suppression amount of a pharmaceutically-acceptable non-toxic salt of the N-m-methoxybenzyl-N,N-dimethyl-N-ethylammonium cation and a pharmaceutically acceptable carrier therefore.

22. The composition of claim 21 in a form for an oral administration.

23. The composition of claim 21 in a form for parenteral administration.

24. The composition of claim 21 in the form of a tablet.

25. The composition of claim 21 in the form of an injectible solution.

26. The composition of claim 21 in which the salt is a chloride, sulphate or sulphonate salt.

27. The composition of claim 21 in which the amount is 100 to 600 mg. of cation.

* * * * *